US010789925B2

(12) United States Patent
Hernandez, Jr.

(10) Patent No.: US 10,789,925 B2
(45) Date of Patent: Sep. 29, 2020

(54) METHOD AND SYSTEM FOR TIMED EVENT EVALUATION

(71) Applicant: Interactive Metronome, Inc., Sunrise, FL (US)

(72) Inventor: Jose M. Hernandez, Jr., Miramar, FL (US)

(73) Assignee: Interactive Metronome, Inc., Sunrise, FL (US)

( * ) Notice: Subject to any disclaimer, the term of this patent is extended or adjusted under 35 U.S.C. 154(b) by 588 days.

(21) Appl. No.: 15/659,810

(22) Filed: Jul. 26, 2017

(65) Prior Publication Data

US 2017/0323625 A1    Nov. 9, 2017

Related U.S. Application Data

(63) Continuation of application No. 14/714,464, filed on May 18, 2015, now Pat. No. 9,747,880.

(60) Provisional application No. 62/005,370, filed on May 30, 2014.

(51) Int. Cl.
| | | |
|---|---|---|
| *G10H 1/40* | (2006.01) | |
| *A61B 5/11* | (2006.01) | |
| *A61B 5/00* | (2006.01) | |
| *A61B 5/16* | (2006.01) | |

(52) U.S. Cl.
CPC ............ *G10H 1/40* (2013.01); *A61B 5/1114* (2013.01); *A61B 5/1124* (2013.01); *A61B 5/1126* (2013.01); *A61B 5/162* (2013.01); *A61B 5/40* (2013.01); *A61B 5/6887* (2013.01); *A61B 5/7475* (2013.01); *A61B 2505/09* (2013.01); *A61B 2562/0219* (2013.01); *G10H 2210/076* (2013.01); *G10H 2220/086* (2013.01); *G10H 2220/371* (2013.01)

(58) Field of Classification Search
USPC ........................................................... 84/484
See application file for complete search history.

(56) References Cited

U.S. PATENT DOCUMENTS

| | | |
|---|---|---|
| 4,919,030 A | 4/1990 | Perron, III |
| 5,529,498 A | 6/1996 | Cassily et al. |
| 5,743,744 A | 4/1998 | Cassily et al. |
| 6,546,134 B1 | 4/2003 | Shrairman et al. |
| 6,719,690 B1 | 4/2004 | Cassily |
| 6,809,721 B2 | 10/2004 | Love |
| 7,122,004 B1 | 10/2006 | Cassily |
| 8,694,663 B2 | 4/2014 | zou et al. |
| 8,968,218 B2 | 3/2015 | Wukasch et al. |

(Continued)

OTHER PUBLICATIONS

International Preliminary Report on Patentability from corresponding Patent Cooperation Treaty Patent Application No. PCT/US2015/031336 dated Dec. 15, 2016.

*Primary Examiner* — Christopher Uhlir
(74) *Attorney, Agent, or Firm* — Gardner, Linn, Burkhart & Ondersma LLP

(57) ABSTRACT

A timing unit and method useable with a computer and user input includes a circuit and a timer. The timer establishes a reference signal having periodic occurrence and receives a trigger signal from the user input. The circuit generates information that represents the periodic occurrences of the reference signal and response timing data representing a relationship between the trigger signal and one of the occurrences. A communication channel is provided between the circuit and the computer.

31 Claims, 14 Drawing Sheets

(56) References Cited

U.S. PATENT DOCUMENTS

| | | |
|---|---|---|
| 2003/0140251 A1 | 6/2003 | Marin et al. |
| 2004/0039705 A1 | 2/2004 | Svancarek et al. |
| 2007/0000374 A1 | 1/2007 | Clark et al. |
| 2009/0043170 A1 | 2/2009 | Sulkin et al. |
| 2010/0217159 A1* | 8/2010 | Wukasch ............. A61B 5/1038 600/595 |
| 2011/0291743 A1 | 12/2011 | Taylor |
| 2013/0027341 A1 | 1/2013 | Mastandrea |
| 2015/0348527 A1 | 12/2015 | Hernandez |

* cited by examiner

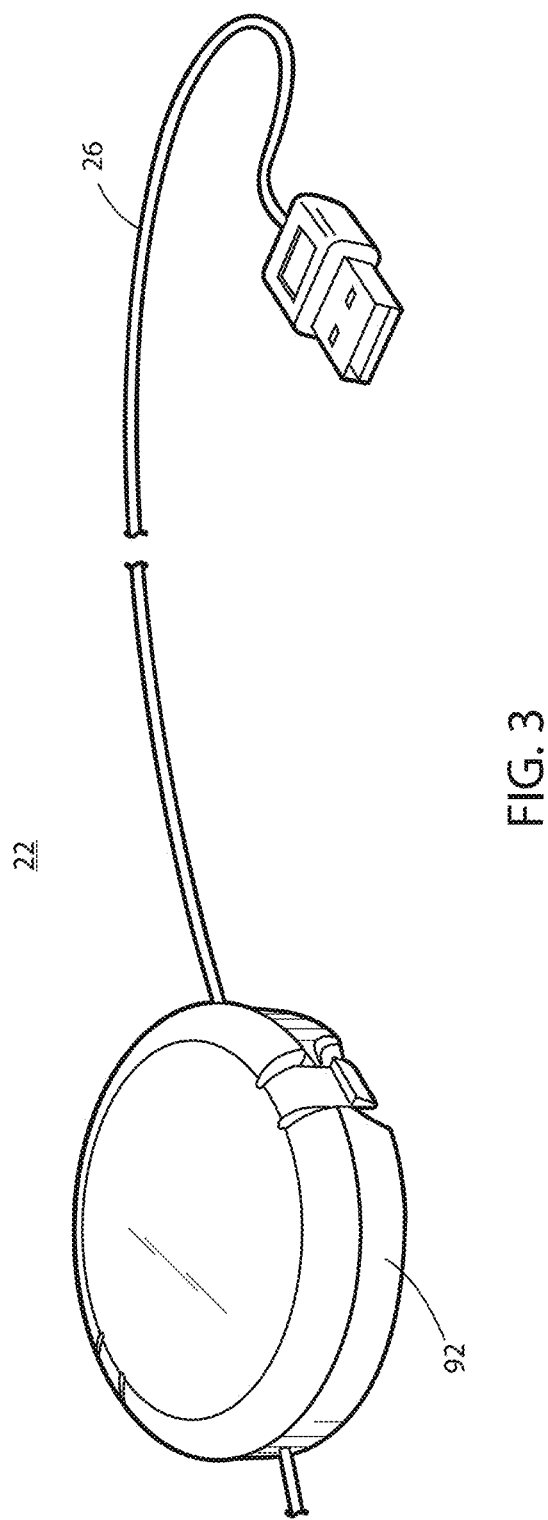

Message Description: Inbound

The sections below describe the different messages that are transmitted by the timing unit and the computing unit. For every command sent, the recipient will acknowledge the message in the form of a PASS/FAIL or actual data being requested. The format of the table depicts the sequence of events or message exchange.

Message START:

This command is utilized for signaling the timing unit to start an exercise. A PASS/FAIL response is returned.

Message STOP:

This command is utilized for signaling the timing unit to stop an exercise. A PASS/FAIL response is returned.

Message PAUSE:

This command is utilized for pausing an active exercise and continuing it from a paused condition. A PASS/FAIL response is returned with the appropriate sub-command included.

Message TEMPO:

This command is utilized for setting the exercise tempo for an exercise. A PASS/FAIL response is returned.

Message SESS_TIME:

This command is utilized for setting the exercise's duration time. A PASS/FAIL response is returned.

Message DIFFICULTY:

This command is utilized for setting the exercise's difficulty level. A PASS/FAIL response is returned.

Message TIME_USED:

This command is utilized for retrieving the total usage time of the timing unit. A response is returned with the time value.

Message FW_VER:

This command is utilized for retrieving the firmware revision number of the timing unit. A response is returned with the firmware revision number.

FIG. 11A

Message SESS_PAR:

This command is utilized for setting the boundary used for sessions as defined by the subcommands. A PASS/FAIL response or value is returned with the appropriate subcommand included.

Message REF_TONE:

This command is utilized for signaling a reference tone being generated by the timing unit. A PASS/FAIL response is returned.

| NGH Command | REF_TONE :: 50$_H$ | | |
|---|---|---|---|
| | SUBCMD | DATA | Description |
| | | *Value | Beat number. |
| HSW Response | | 00$_H$ | Message error. |
| | | | Message acknowledged. |

* Value: this field is 4 bytes long

Message TRIGGER_DATA:

This command is utilized for signaling a trigger event occurrence on the timing unit. A PASS/FAIL response is returned.

| NGH Command | TRIGGER_DATA :: | | |
|---|---|---|---|
| | SUBCMD | DATA | Description |
| | | *Value | Beat Number |
| | | | Trigger Source |
| | | 01$_H$ | Hand |
| | | 02$_H$ | Foot |
| | | *Value | Trigger time elapsed. |
| | | | Time Zone |
| | | 01$_H$ | Very early |
| | | 02$_H$ | Early |
| | | 03$_H$ | Late |
| | | 04$_H$ | Very Late |
| HSW Response | | 00$_H$ | Message error. |
| | | 01$_H$ | Message acknowledged. |

* Value: this field is 2 bytes long, all other fields are 1 byte long.

Message SESS_END:

This command is utilized for signaling the completion of a session by the timing unit. A PASS/FAIL response is returned.

FIG. 11B

Message TEMPO_CAL:

This command is utilized for signaling the computing unit that the timing unit is presently synchronizing the tempo timing.

FIG. 11C

METHOD AND SYSTEM FOR TIMED EVENT EVALUATION

CROSS REFERENCE TO RELATED APPLICATION

The present application is a continuation of U.S. patent application Ser. No. 14/714,464, filed May 18, 2015, which claims priority from U.S. provisional patent application Ser. No. 62/005,370, filed May 30, 2014, the disclosure of which is hereby incorporated herein by reference in its entirety.

BACKGROUND OF THE INVENTION

The present invention is directed to evaluating timed events and, in particular, to measuring a human's ability to rhythmically stay on a beat. While the invention is illustrated for use in carrying out a technique for improving neurological functionality, it may have other applications as well.

Generating a rhythmic beat and measuring a human response in attempting to clap hands or stomp a foot in synchronism with the beat is difficult. Time beat generation and response time measuring should be achieved to sub-millisecond accuracy. Current computing devices, such as laptop and tablet computers, Smartphones, and the like, build in too much latency in generating output signals and responding to input signals. While specialized hardware circuits perform better than programmed computers, they still introduce bias which is variable and, therefore, difficult to compensate for. Moreover, specialized hardware circuits tend to be inflexible and prone to frequent configuration changes that need to be back-fitted in the field.

SUMMARY OF THE INVENTION

The present invention provides a solution to the difficulty of accurately measuring "response timing". Response timing, as used herein, is the human ability to maintain a rhythmic and synchronized beat over a period of time. Research has linked this rhythmic ability to a person's language skills, working memory, auditory processing and other neurological skills. Response timing may be measured by presenting a reference signal, or beat, to a human and obtaining a trigger response from the user that represents the user's anticipation of the occurrence of the reference signal along with generation of a guidance signal that is presented to the user for the purpose of guiding the user into synchronism with the reference signal. Such techniques require very precise time measurements that greatly exceed the capability of present commercially available computing units, such as laptop computers, tablet computers, cell phones, and the like. The present invention is embodied in a system that is capable of such accurate timing while providing exceptional flexibility in adaptation to various applications without the need to supply various versions of the hardware.

A timing unit and method useable with a computer and user input, according to an aspect of the invention, includes a circuit and a timer. The timer establishes a reference signal having periodic occurrence and receives a trigger signal from the user input. The circuit generates information that represents the periodic occurrences of the reference signal and response timing data representing a relationship between the trigger signal and one of the occurrences. A communication channel is provided between the circuit and the computer.

A timed event evaluation system and method, according to an aspect of the invention, includes a timing unit in combination with a computing unit having an audible and a visual output. The timing unit has a circuit that responds to a user input. The circuit defines a timer. The timer establishes a reference signal having periodic occurrences and receives a trigger signal from the user input. The circuit supplies information that represents the periodic occurrences of the reference signal and response timing data representing a relationship between each trigger signal and one of the occurrences. The computing unit receives information from the timing unit and provides the occurrences of the reference signal to the user with the audible output and provides the relationship between the reference signal and the trigger signal to the user with the audible output and/or the visual output.

A timing unit that is useable with a user input, according to an aspect of the invention, includes a timer and a circuit. The circuit is responsive to the timer to establish a reference signal having periodic occurrences and receives a trigger signal from the user input. The circuit runs a program and has an interrupt generator. The interrupt generator is responsive to the user input to interrupt the program in response to operation of the user input and to record a value of the timer when the trigger signal occurs. The circuit formats response timing data representing a relationship between the timer when the user input occurs and one of the occurrences. The response timing data may be provided to a computer that produces an output to the user. The output may be audible and/or visual. The circuit may further include another interrupt generator that is responsive to the timer and interrupts the program after the passage of a defined period of time. The circuit formats an occurrence of a reference signal in response to the another interrupt generator. The data representing the occurrence of the reference signal may be provided to the computer that produces an audible tone, such as a "beat" to the user.

A method of generating response timing data representing a relationship between a time when a user operation of a user input occurs and an occurrence of a reference signal using a circuit operating a program, the time representing an output of a timer when the user operates the user input, according to an aspect of the invention, includes receiving a trigger signal with the circuit from the user operation of the user input and interrupting the program in response to the trigger signal. The circuit records a value of the time output when the user input occurs. The circuit formats response timing data representing a relationship between the time output when the trigger signal occurs and one of the occurrences of the reference signal and provides the response timing data. The method may further include generating an occurrence of the reference signal with the circuit in response to the time output of the timer including interrupting the program in response to passage of a particular interval of time generated with the time output. The circuit formats data representing an occurrence of a reference signal as the value of the time output at the passage of the particular time interval.

These and other objects, advantages and features of this invention will become apparent upon review of the following specification in conjunction with the drawings.

BRIEF DESCRIPTION OF THE DRAWINGS

FIG. 3 is a perspective view of a timing unit;

FIGS. 11a-11c are a table illustrating data flow between the timing unit and the host computing unit.

DESCRIPTION OF THE PREFERRED EMBODIMENT

Figure 1:
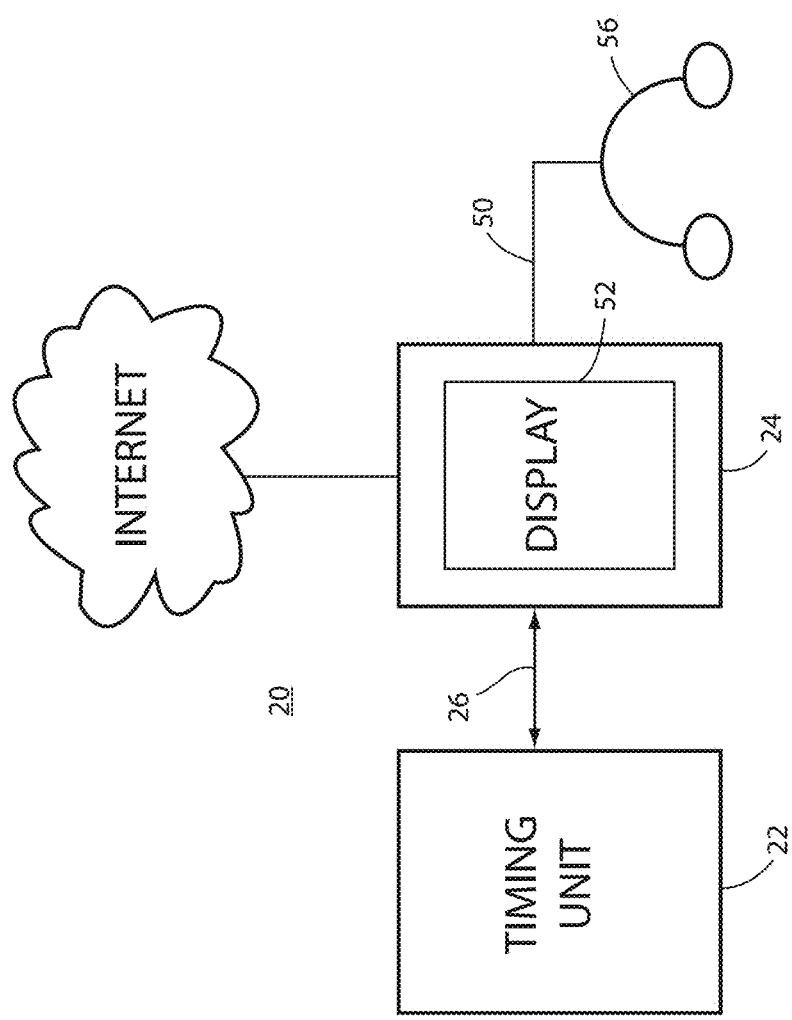
FIG. 1 is a block diagram of a timed event evaluation system according to an embodiment of the invention.
Figure 4:
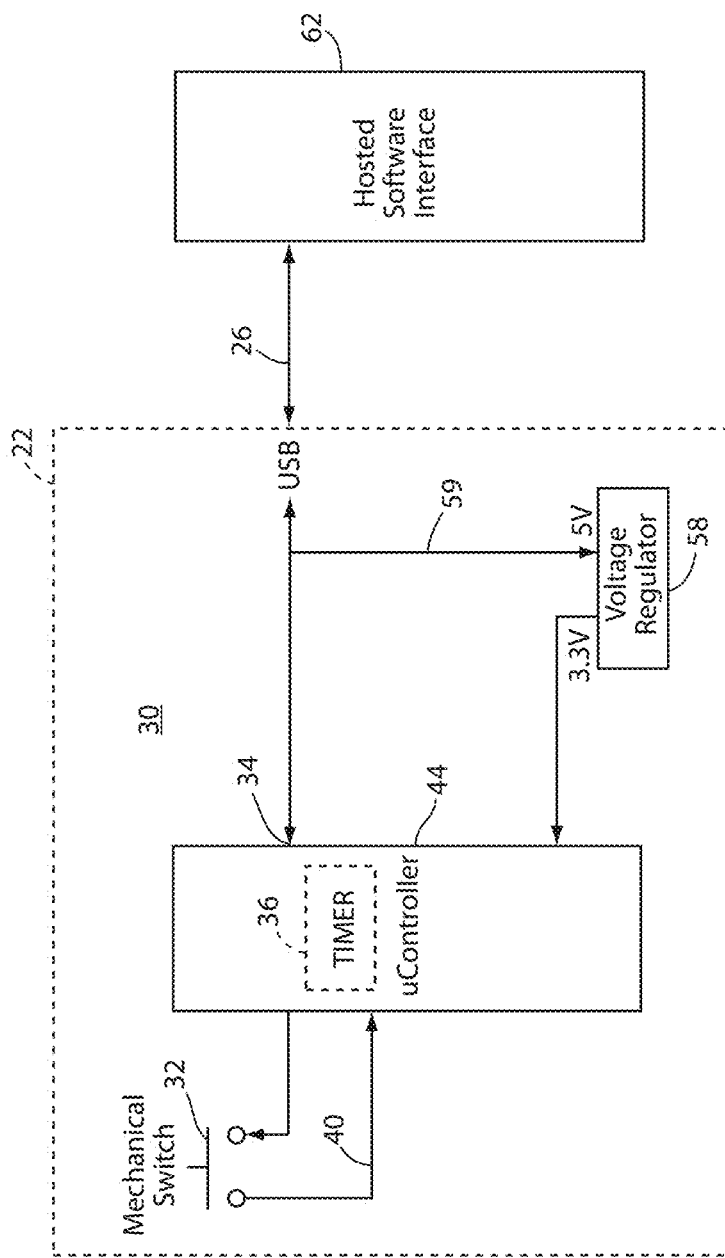
FIG. 4 is a block diagram of the electrical schematic of the system in FIG. 1.

Referring now to the drawings and the illustrative embodiments depicted therein, a timed event evaluation system 20 includes a timing unit 22, a computing unit 24 and a communication channel 26 between the timing unit and the computing unit (FIG. 1). Timing unit 22 has a circuit 30 and a user input 32 (FIG. 4). Circuit 30 runs a program 46 and defines a communication port 34 and a timer 36. Timer 36, which is in the form of a programmed microprocessor 44 that is incorporated with circuit 30, generates a reference signal 38 having a periodic occurrence. Such periodic occurrence forms a "beat" to which the user, or patient, attempts to respond by operating input 32 in unison with occurrences of the reference signal, as disclosed in commonly assigned U.S. Pat. Nos. 5,529,498 and 5,743,744, the disclosures of which are hereby incorporated herein by reference. Microprocessor 44 receives a trigger signal 40 from user input 32. Communication port 34 supplies information 42 that represents the periodic occurrences of the reference signal as well as a relationship between each trigger signal received from user input 32 and one of the occurrences of the reference signal. The information 42 supplied on communication port 34 is generated by microprocessor 44.

Figure 2:
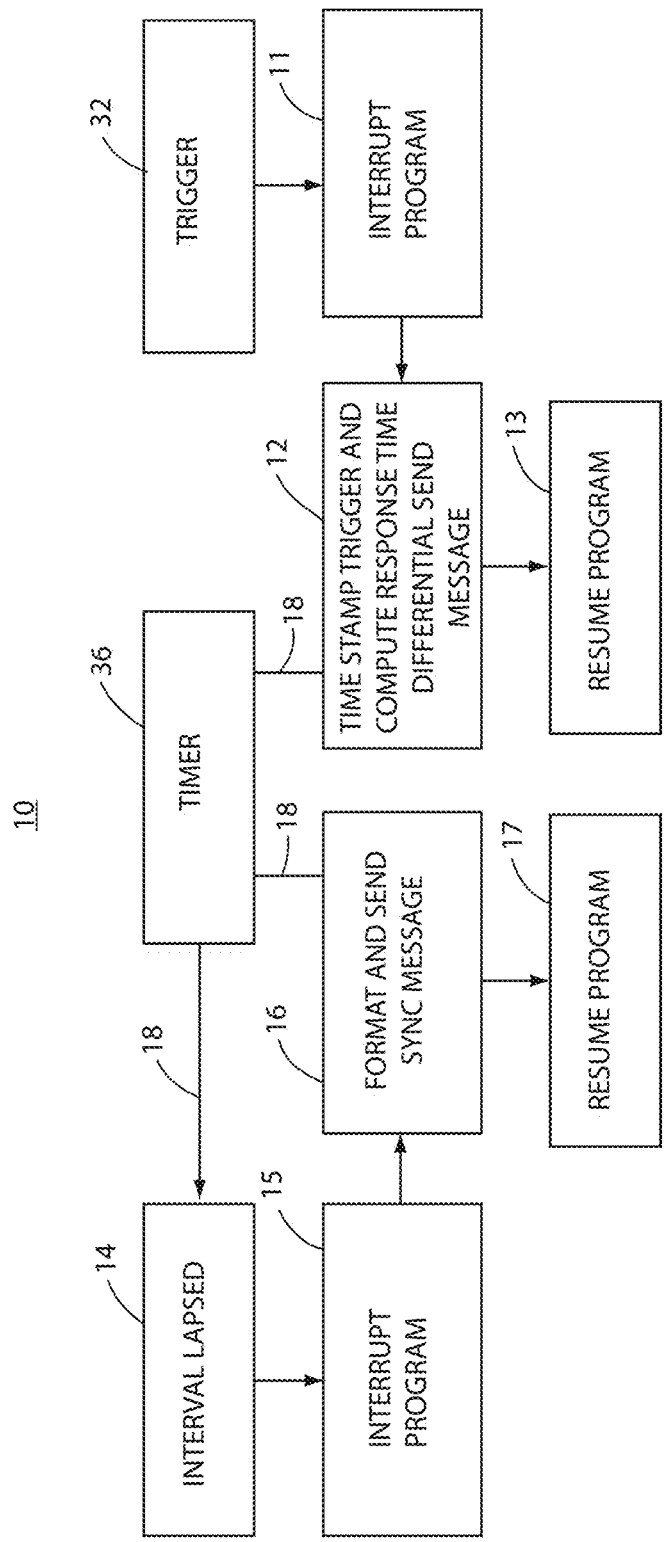
FIG. 2 is a block diagram of a process carried out by the timing unit.

Referring now to FIG. 2, an interrupt generator process 10 is responsive to the user input 32 to interrupt a program 46 at 11 in response to operation of the user input and to record at 12 a value of timer 36 when the trigger signal occurs. Circuit 30 formats response timing data representing a relationship between the timer when the user input occurs and one of the occurrences. The response timing data may be provided to computing unit 24 which produces an output to the user, as will be discussed in more detail below. The program 46 is resumed at 13. Process 10 may further include another interrupt generator that is responsive to timer 36 and interrupts the program at 15 after the passage of a defined period of time as indicated at 14. The circuit formats an occurrence of a reference signal at 16 in response to the another interrupt generator. The data representing the occurrence of the reference signal may be provided to the computer that produces an audible tone, such as a "beat" to the user. Program 46 is resumed at 17.

Computing unit 24 has an audible output 50 and a visual output 52. Computing unit 24 receives the information supplied by communication port 34 of timing unit 22. Computing unit 24 includes a user application program 62 that decodes the information 42 and provides occurrences of the reference signal to the user with audible output 50. Computing unit 24 also provides the relationship between each trigger signal received from user input 32 and one of the occurrences of the reference signal. This relationship is supplied either in the form of audible data from audible output 50 and/or as video data from visual output 52. Audible output 50 is supplied to one or more audio speakers, such stereophonic headphones 56. Visual output 52 is in the form of a display device that is supplied with computing unit 24. Computing unit 24 is a commercially available consumer device, such as a desktop personal computer or, more likely, a portable consumer device, such as a laptop personal computer, a tablet computer, or a data ("smart") cell phone.

Communication channel 26 supplies the information 42 from communication port 34 of timing unit 22 to computing unit 24 and supplies control data from computing unit 24 that is used to control timing unit 22, as will be discussed in more detail below. In the illustrated embodiment, communication channel 26 is a universal serial bus (USB). As is known in the art, such USB channel is capable of supplying low voltage DC, such as 5 VDC to provide electrical power to timing unit 22. Such low voltage DC is supplied via a power line 59 to a voltage regulator 58 of timing unit 22, which, in turn, supplies a regulated 3.3 VDC to microprocessor 44 and other components of circuit 30. Although communication channel 26 is illustrated as a hard-wired USB bus, at least some of its functions could be performed by a wireless interface of the type that is known in the art. Such additional wireless interfaces may include Bluetooth or other RF or IR communication techniques.

Figure 9:
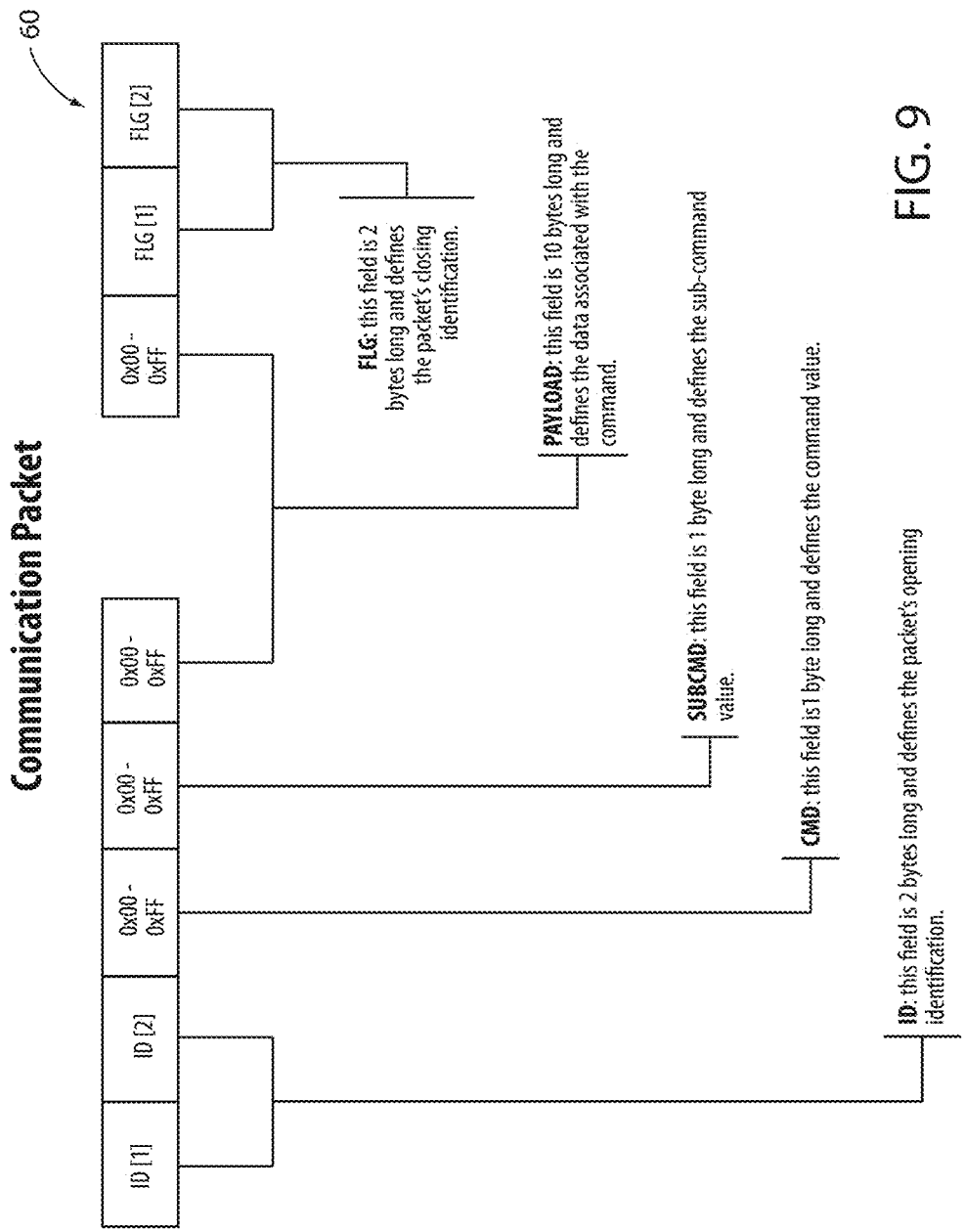
FIG. 9 is a data packet diagram.
Figure 10:
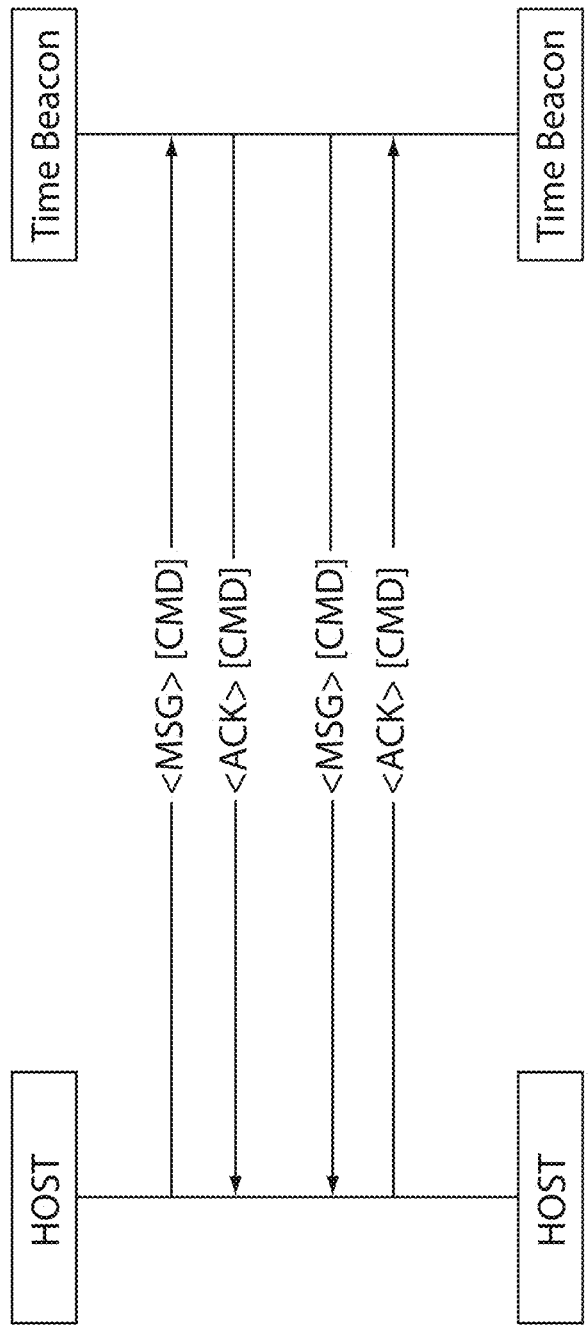
FIG. 10 is a communication handshake between the timing unit and the host computing unit.

Information 42 is formatted into data packets 60 (FIG. 9.). As seen in FIG. 9, data packets 60 conform to protocol of the communication channel used and provide data that allows computing unit 24 to precisely supply the reference signal to audible output 50 for presentation to the user as well as the relationship between each occurrence of the reference signal and the operation of the user input 32. Computing unit 22 runs a user application program 62. User application program 62 controls the manner in which audible output 50 and/or visual output 52 presents to the user the relationship between the occurrences of the reference signal and operation of user input 32. For example, one particular video theme may be used for sports applications and a different theme for a therapeutic neurological setting. Yet a different video theme may be used if the user is a young child. Thus, timed evaluation system 20 may be customized to various applications depending upon the user application program 62 that is installed on computing unit 22. Computing unit 22 may be capable of downloading user application program 62 from a wide area network, such as the Internet. In this manner, timed evaluation system 20 may utilize "cloud" storage as is known in the art to supply a particular application program that is chosen from among a catalog of programs 62 stored in cloud storage.

Timing unit 22 generates a product key 64, such as a particular data value, with communication port 34. Computing unit 24 received the product key 64 and responds to a particular value of the product key by running the user application program 62 if that version of the user application program corresponds to that particular value of the product key. Thus, user application program 62 will function to present the relationship between the user operation of user input 32 and occurrence of reference signal 38 if a correct match occurs between the value of product key 64 and a version of user application program 62 stored at computing unit 24. Conversely, computing unit 24 responds to the absence of a match between product key 64 and the version of application program 62 by not running the user application program to present the relationship to the user. This use of timing unit 22 to generate product key 64 allows the supplier of timing unit 22 to retain control of the user application program 62 that will function with computing unit 24. In this manner, the supplier can supply one version of timing unit 22 for a particular application, such as neurological therapy, and another version of the timing unit for sports use merely by programming a different value of the product key into the timing unit, but without changing hardware. Also, the supplier can make upgrades to user application programs 62 and save those upgrades to the Internet via cloud storage and thereby allow the user of timed evaluation system 20 to download a current version of the application program that corresponds with the intended use of the system that corresponds to the value of product key 64. If communication channel 26 is wireless, the product key may be supplied via a solid-state storage device that is adapted for insertion in the USB port of computing unit 24. Also, with a wireless communication channel 26, voltage regulator 58 will be supplied via batteries or other portable power source. Thus, the use of a hard-wired communication channel 26 supplies various functions that would have to be otherwise achieved if a wireless communication channel is used.

Figure 7:
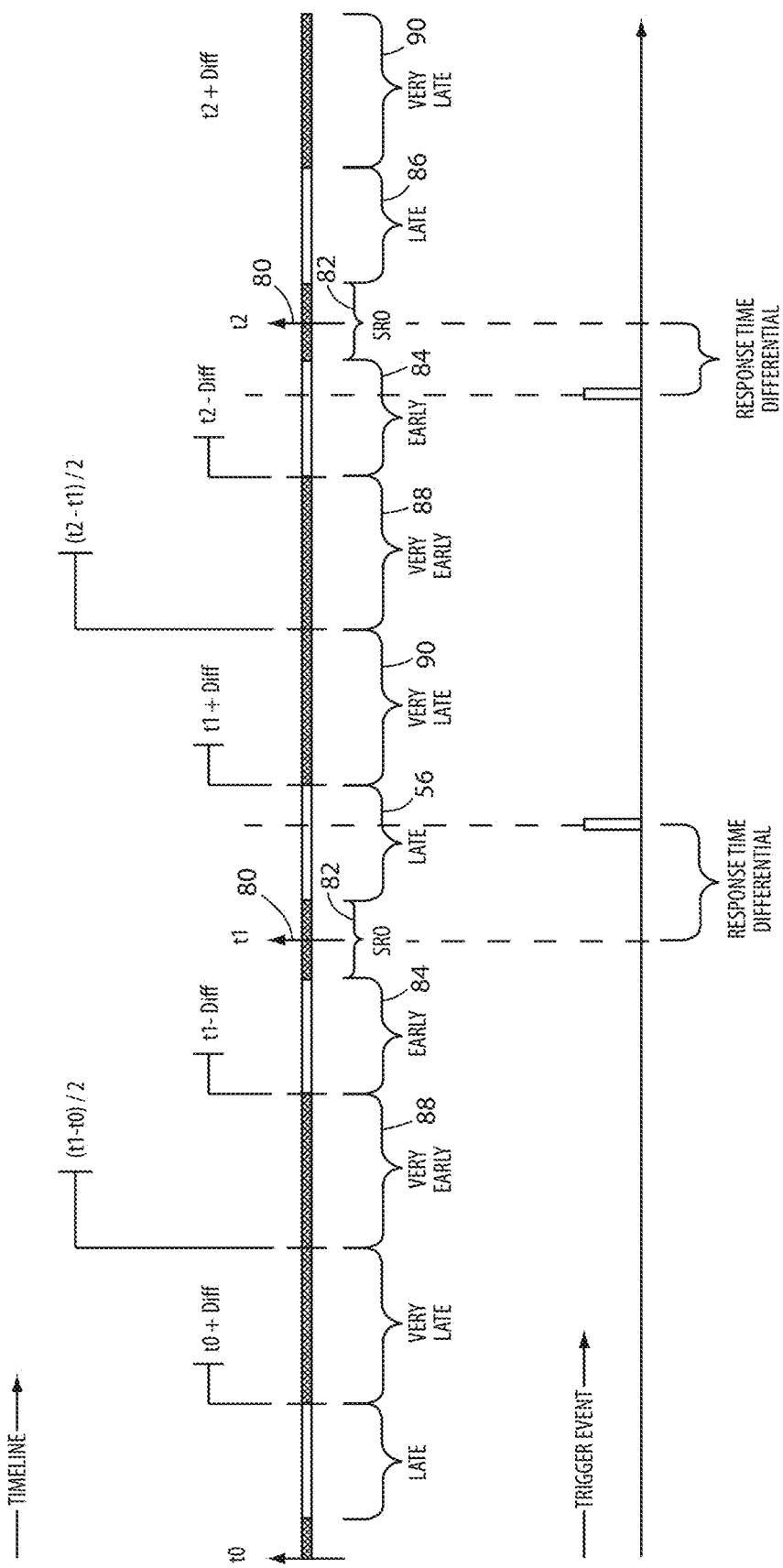
FIG. 7 is a time chart of the timer.

In addition to timing unit 22 supplying information 42 to computing unit 24 that represents the periodic occurrences of the reference signal and the relationship between the user operation of user input 32, computing unit 24 generates control data 66 that controls operation of timer 36 of timing unit 22. Computing unit 24 communicates the control data 66 over communication channel 26. Control data 66 causes timing unit 22 to selectively start and stop timer 36. Control data 66 determines a boundary for performance difficulty. For example, each occurrence 80 of the reference signal is surrounded by "right on" or excellent intervals 82 that define a time tolerance in which user operation of user input 32 is deemed to be ideal (FIG. 7). An "early" and "late" interval 84, 86 establish time intervals in which user operation of input 32 is either earlier, or later than right on interval 82, but not as early/late as very early interval 88 or very late interval 90. Control data 66 instructs timing unit 22 on the duration of each interval 82-90 and thus how accurate a user input must be to fall within a particular interval. The interval 82-90 in which a response falls determines the type of sound produced by audible output 50 to help draw the user into synchronism with occurrences of reference signal 38. As disclosed in the earlier-referenced commonly assigned patents, the sound produced by audible output 50 is supplied to the user concurrently with the user's operation of user input 32. In addition to supplying data as to the interval in which a user input falls, information 42 supplies the response time differential between each beat and user response so that, for example, computing unit 24 can keep a cumulative response time differential for an exercise.

Figure 3A:
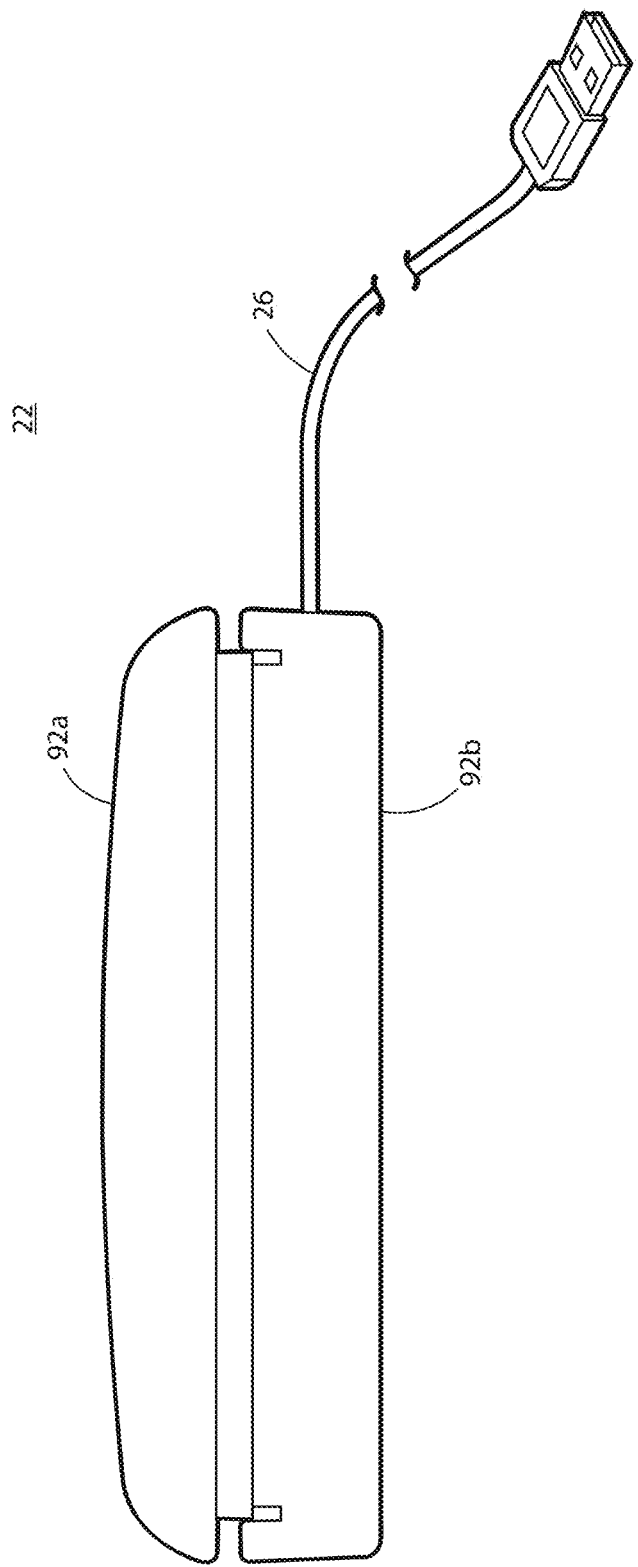
FIG. 3a is a side elevation of the timing unit in FIG. 3.
Figure 8:
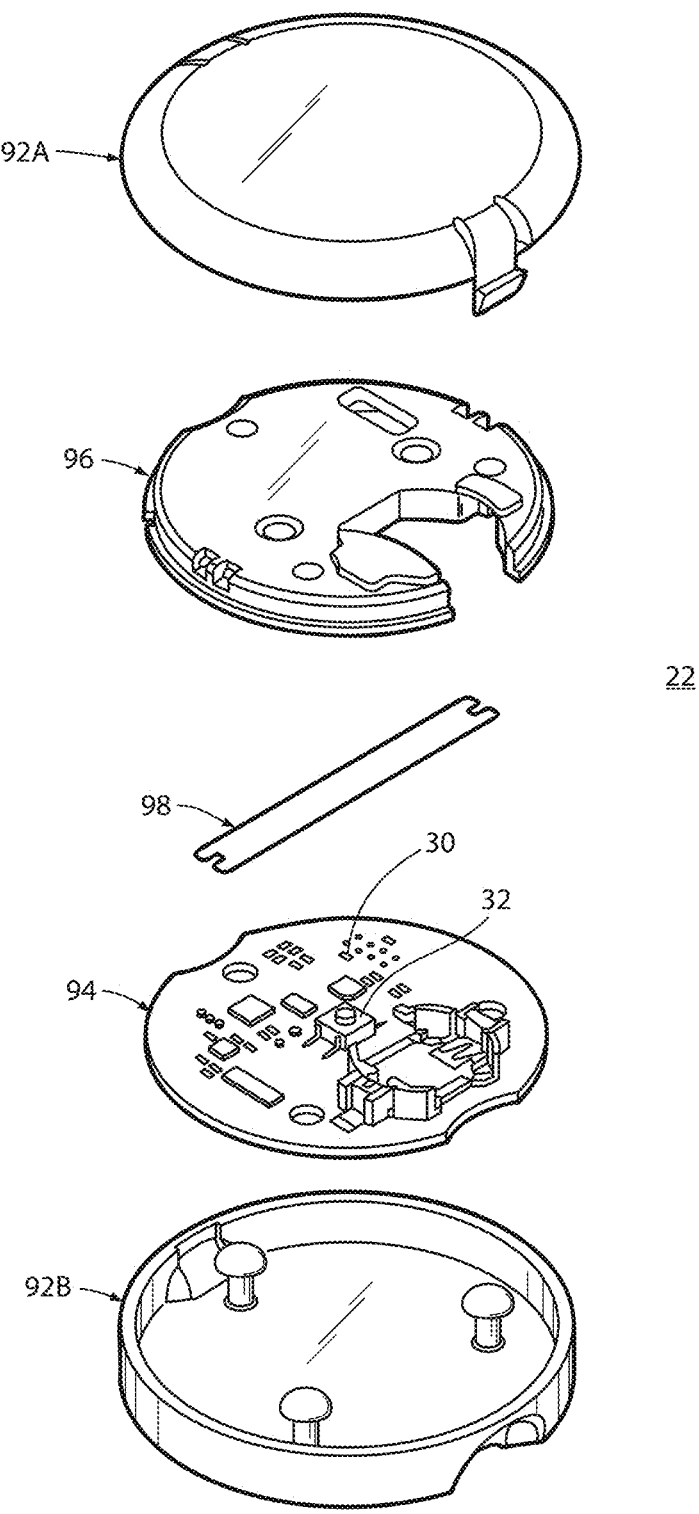
FIG. 8 is an exploded perspective view of a mechanical assembly of the timing unit.

Timing unit 22 includes a housing 92 having housing portions 92a, 92b that together house circuit 30 (FIGS. 2, 3 and 8). Relative motion between housing portions 92a, 92b operate user input 32. Circuit 30 and user input 32, which is illustrated as a mechanical switch but could alternatively be an electronic switch such as an accelerometer, or the like, of the type known in the art, are on a common circuit board 94. A cover 96 protects circuit 30 and user input 32 and a leaf spring 98 returns housing portions 92a, 92b to the non-actuated position for user input 32. A strap (not shown) can be provided on one of housing portions 92a, 92b for attachment to a user's hand. In this manner, timing unit 22 can be a hand-trigger that includes all of the electronics and mechanics to supply accurate timing information to computing unit 24. Alternatively, timing unit 22 can be a foot-trigger to monitor user input in the form of foot tapping. In this manner, accurate timing can be provided without requiring that computing unit 24 be capable of accurately generating occurrences of a reference signal and accurately measuring user response to same.

Figure 5:
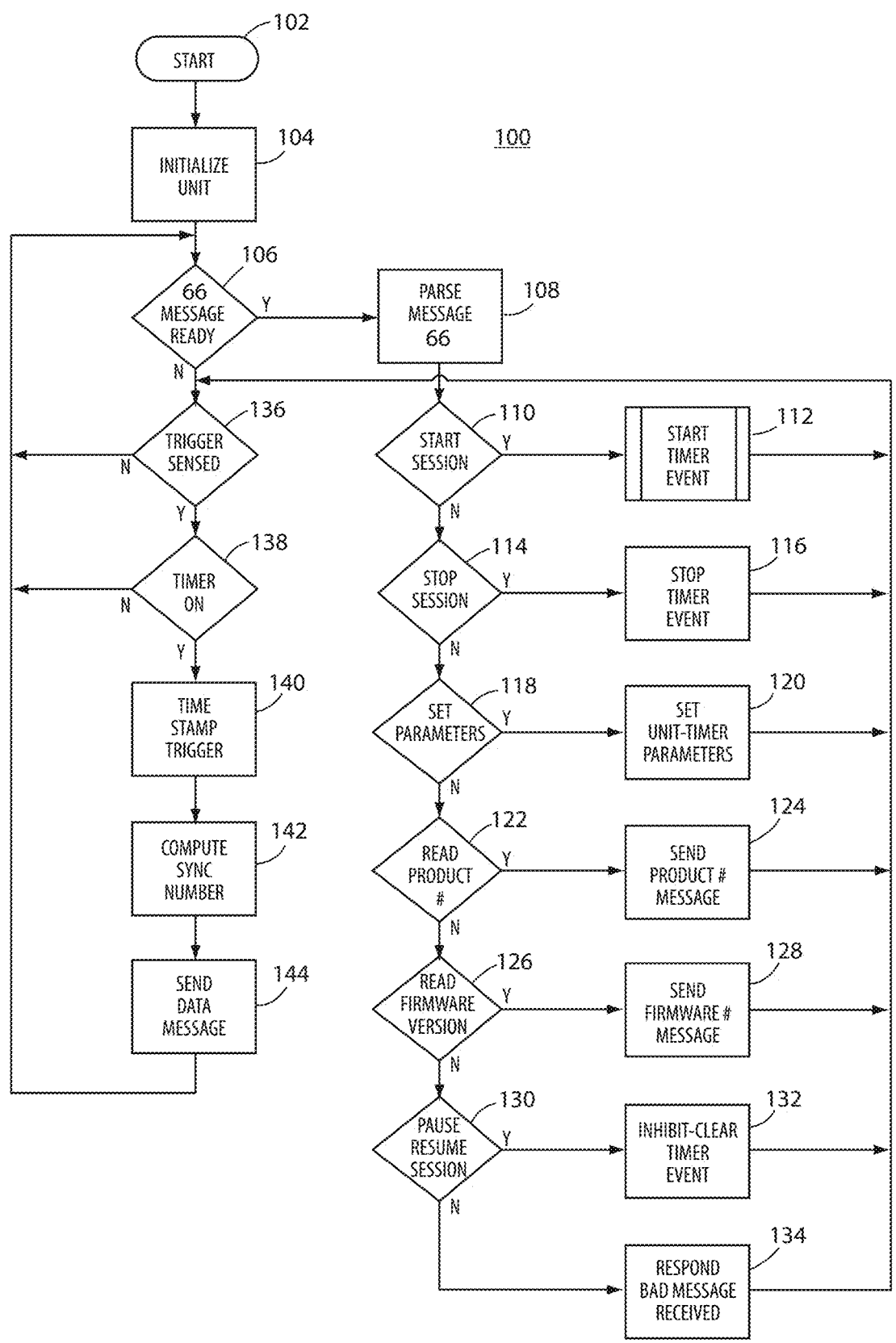
FIG. 5 is a flow chart of an administrative program run by the timing unit.

Microprocessor 44 of timing unit 22 runs a main loop administrative algorithm 100 (FIG. 5). Algorithm 100 starts at 102 by performing an initialization routine 104 whenever power is applied to voltage regulator 58. A determination is made at 106 as to whether control data 66 has been received and, if so, the data is parsed at 108. It is then determined at 110 whether the control data is to start timer 36 and, if so, a start event 112 starts the timer. If not, then it is determined if the control data is to stop a running timer 36 and, if so, a stop event 116 stops the timer. If not, it is determined at 118 whether the control data is to establish the performance difficulty of the timing unit. If so, new timing parameters are set at 120 in order to set the widths of time intervals 82-90. If not, then it is determined at 122 whether the computing unit is requesting a product key 64 be sent by the timing unit in order to determine the type of user application program 62 that the computing unit is entitled to run, or the like. If so, communication port 34 sends a product key 64 to the computing unit at 124. If not, then it is determined at 126 whether the computing unit is requesting the firmware version that is being run by microcomputer. If so, then communication port sends a message containing the firmware version being run by microprocessor 44 so that computing unit 24 can determine if a later version is available so that the firmware run by the microprocessor should be updated. Computing unit 24 can download to microprocessor 44 updated firmware over communication channel 26 using conventional techniques.

If it is determined at 126 that the computing unit has not requested the firmware version, it is determined at 130 whether the user has activated a "pause" function to pause the exercise being performed. If so, an inhibit event is carried out at 132 to inhibit running of timer 36. If it is determined at 130 that no pause function is requested, it is determined at 134 that an invalid control data message was received and no action is taken. Control then passes to 136 for microprocessor 44 to await receipt of a trigger event caused by the user operating user input 32. Similarly, if no control data is received from computing unit 24, control passes to 136.

When it is determined at 136 that a trigger event has been received as a result of the user operating user input 32, it is determined at 138 whether timer 36 is running. If so, it is recorded at 140 the time "tick" when the user input is operated and a "sync" or response time differential number is calculated. The sync number is the interval 82-90 in which the trigger occurred and the timing tick within that interval when the trigger occurred. Microprocessor 44 creates information data packet 42 which informs the computing unit 24 of the period in which the trigger occurred, the precise tick of the trigger, and the time that the reference signal occurred. This allows the computing unit to present the reference signal to the user concurrently with operation of the user input via audible output 50 as well as to give guidance to the user concurrently with the trigger occurring via audible output 50 and/or visual output 52, whether the trigger was very early, early, right on, late or very late. This is for the purpose of drawing the user operation of input 32 into synchronism with occurrences of reference signal 38. After the sync number is computed at 142, a data packet 42 is formatted and communicated at 144 to computing unit 24 over communication channel 26.

Figure 6:
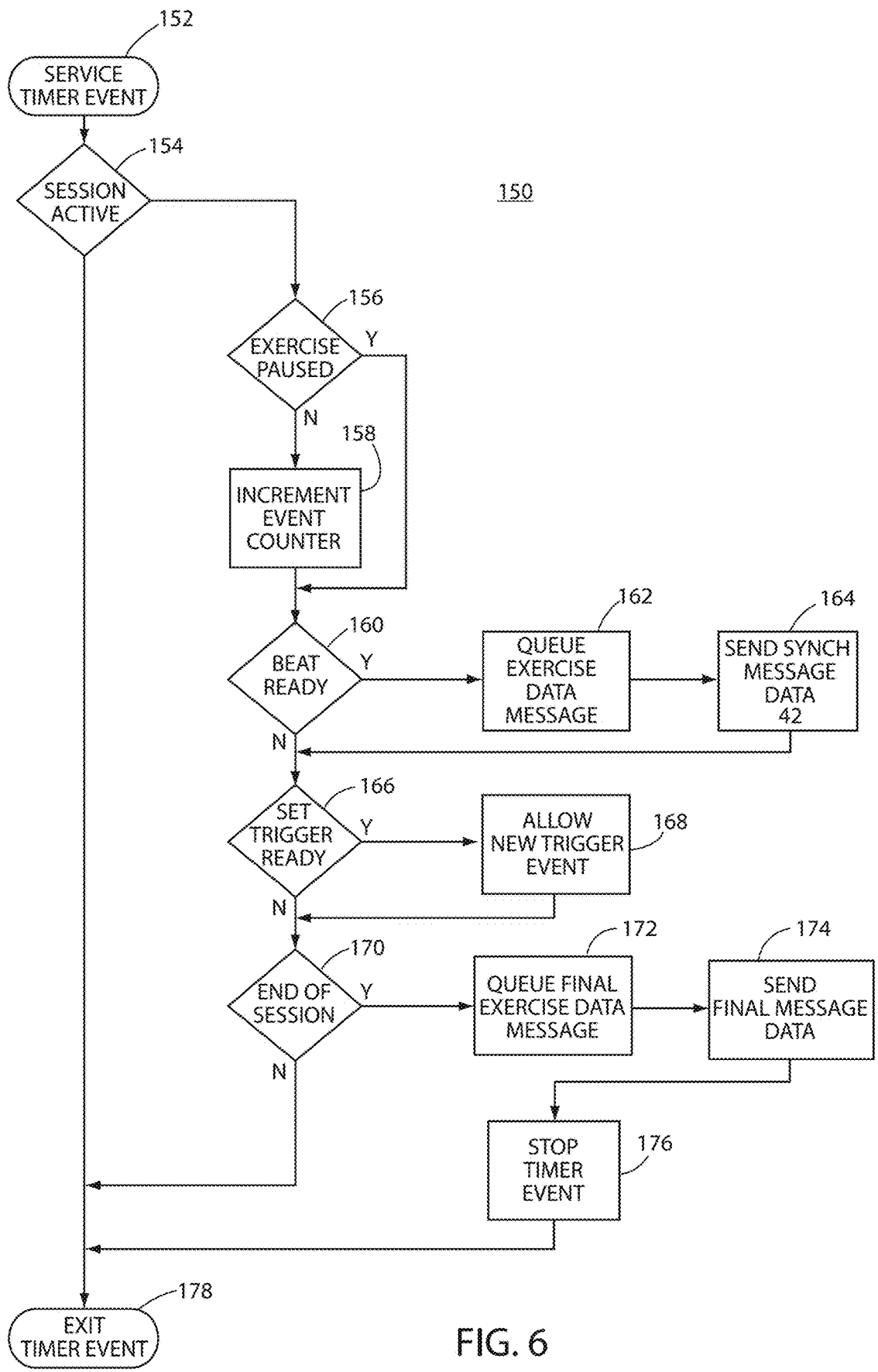
FIG. 6 is a flow chart of a timer loop program run by the timing unit.

Microcomputer 44 defines and operates timer 36 using a timer event routine 150 (FIG. 6) which begins at 152 by determining at 154 whether the start timer event 112 has occurred. If so, and if it is determined at 156 that the user has not paused the exercise, a very precise clock is incremented by one tick at 158 as previously described. It is determined at 160 if a reference signal occurrence 80 has happened. If so, a data packet is created at 162 and sent to computing unit 24 at 164 of the occurrence of the reference signal along with the number of that particular beat so that the reference signal occurrence, or beat, can be presented to the user. If the reference signal is not occurring during that pass through the software, it is determined at 166 whether user input 32 is prepared to be actuated by the user. This requirement that the user input 32 be ready provides a de-bounce function to ensure that input 32 is released each time and not held in an actuated position. If it is determined at 166 that a user trigger can be received, the routine accepts a new trigger at 168 if it occurs during that pass through the routine.

Assuming the exercise session has not ended at 170, the trigger event, if it occurs, causes the program to be interrupted and a data packet is formatted and sent to computing unit 24. The program is then resumed. If it is determined at 170 that a stop timer event 116 has been received, final messages are formatted at 172 and sent to the computing unit at 174. The timer is stopped at 176 and the timer event exited at 178. If the timer event is not started, a continuous loop from 152 to 178 occurs. In the illustrated embodiment, each tick is equal to 1 millisecond although a greater or lesser amount of time may be used.

Routines 100 and 150 are stored in firmware of circuit 30 so that the timing unit is available for operation as soon as it is connected with the USB port of computing unit 24. In the illustrated embodiment, the microprocessor is of the type marketed by Atnel under Model No. AT91SAM7S. Of course, microprocessor 44 may be supplied from other sources or any type of programmable digital device, such as programmable gate array, integrated circuit, or the like.

While the foregoing description describes several embodiments of the present invention, it will be understood by those skilled in the art that variations and modifications to these embodiments may be made without departing from the spirit and scope of the invention, as defined in the claims below. The present invention encompasses all combinations of various embodiments or aspects of the invention described herein. It is understood that any and all embodiments of the present invention may be taken in conjunction with any other embodiment to describe additional embodiments of the present invention. Furthermore, any elements of an embodiment may be combined with any and all other elements of any of the embodiments to describe additional embodiments.

The embodiments of the invention in which an exclusive property or privilege is claimed are defined as follows:

1. A timing unit for use with a commercially available consumer device separate from said timing unit to supply to a user occurrences of a reference signal and differential between a trigger signal and an occurrence of said reference signal including a performance difficulty interval into which the differential falls to draw the user into synchronism with occurrences of the reference signal, said timing unit comprising:

a housing, a user input device adapted to generate a trigger signal when activated by a user and a circuit, said circuit and said user input device housed by said housing, said circuit comprising a programmable digital device defining a timer, a program, and a communication port, said program being responsive to said timer and said user input device and adapted to generate reference signal data and response timing data, said reference signal data representing periodic occurrences of a reference signal generated by said timer, said response timing data made up of a differential between a trigger signal and an occurrence of said reference signal and which one of a plurality of performance difficulty intervals the differential falls wherein ranges of the performance difficulty intervals established by difficulty data; and said communication port adapted to connect with a communication channel to communicating reference signal data and response timing data to the consumer device and receive control data including difficulty data from the consumer device.

2. The timing unit as claimed in claim 1 wherein said communication port is hard wired or wireless.

3. The timing unit as claimed in claim 1 wherein said program having an interrupt generator, said interrupt generator being responsive to the trigger signal to interrupt the program in response to operation of the user input device and to record a value of the timer when the trigger signal occurs, wherein said circuit formats response timing data representing a relationship between the timer when the trigger signal occurs and one of the occurrences.

4. The timing unit as claimed in claim 3 wherein said circuit includes another interrupt generator that is responsive to the timer and interrupts the program after passage of a defined period of time and wherein said circuit formats data representing an occurrence of a reference signal in response to the another interrupt generator.

5. The timing unit as claimed in claim 1 wherein said reference signal data and response timing data are formatted as data packets.

6. The timing unit as claimed in claim 1 wherein the performance the difficulty intervals comprise an excellent band, an early band, a very early band, a late band, and a very late band.

7. The timing unit as claimed in claim 1 wherein said housing comprises housing portions that house said circuit and said user input device, wherein relative motion between said housing portions operate said user input device.

8. The timing as claimed in claim 7 wherein said circuit and said user input device are on a common circuit board.

9. The timing unit as claimed in claim 1 wherein said programmable digital device comprises one chosen from a microprocessor, a programmable gate array, and an integrated circuit.

10. A timing system for measuring response timing, comprising:

a timing unit having a housing, a user input device adapted to generate a trigger signal when activated by a user and a circuit, said circuit and said user input device housed by said housing, said circuit comprising a programmable digital device defining a timer, a program and a communication port, said program being responsive to said timer and said user input device and adapted to generate reference signal data and response timing data, said reference signal data representing periodic occurrences of a reference signal generated by said timer, said response timing data made up of a differential between a trigger signal and an occurrence of said reference signal and which one of a plurality of performance difficulty intervals the differential falls wherein ranges of the performance difficulty intervals established by difficulty data;

a commercially available consumer device separate from said timing unit, said consumer device comprising a computer and having an audible output and a visual output, said consumer device programmed with an application program that is adapted to receive and decode the reference signal data and response timing data from said timing unit to supply to a user occurrences of said reference signal and differential between a trigger signal and an occurrence of said reference signal including which performance difficulty interval the differential falls to draw the user into synchronism with occurrences of the reference signal;

said consumer device generating control data used by said program to at least establish a value of said difficulty data; and a communication channel between said communication port and said consumer device, said communication channel communicating reference signal data and response timing data from said timing unit to said consumer device and control data from said consumer device to said timing unit.

11. The timing system as claimed in claim 10 wherein said program having an interrupt generator, said interrupt generator being responsive to the trigger signal to interrupt the program in response to operation of the user input device and to record a value of the timer when the trigger signal occurs, wherein said circuit formats response timing data representing a relationship between the timer when the trigger signal occurs and one of the occurrences.

12. The timing system as claimed in claim 11 wherein said circuit includes another interrupt generator that is responsive to the timer and interrupts the program after passage of a defined period of time and wherein said circuit formats data representing an occurrence of a reference signal in response to the another interrupt generator.

13. The timing system as claimed in claim 10 wherein said programmable digital device comprises one chosen from a microprocessor, a programmable gate array, and an integrated circuit.

14. The timing system as claimed in claim 10 wherein said consumer device comprises a portable consumer device.

15. The timing system as claimed in claim 14 wherein said portable consumer device comprises one chosen from a laptop personal computer, a tablet computer, and a data phone.

16. The system as claimed in claim 10 wherein said reference signal data and response timing data are formatted as data packets.

17. The system as claimed in claim 10 wherein said application program controlling a manner in which at least one chosen from said audible output and said visual output is configured for presenting said differential and performance difficulty interval to a user.

18. The system as claimed in claim 10 wherein the performance difficulty intervals comprise an excellent band, an early band, a very early band, a late band, and a very late band.

19. The system as claimed in claim 10 wherein said timing unit comprises a housing having housing portions that house said circuit and said user input device, wherein relative motion between said housing portions operate said user input device.

20. The system as claimed in claim 19 wherein said circuit and said user input device are on a common circuit board.

21. A timing system for measuring response timing, comprising:

a timing unit having a housing, a user input device adapted to generate a trigger signal when activated by a user and a circuit, said circuit and said user input device housed by said housing, said circuit comprising a programmable digital device defining a timer, a program and a communication port, said program being responsive to said timer and said user input device and adapted to generate reference signal data and response timing data, said reference signal data representing periodic occurrences of a reference signal generated by said timer, said response timing data made up of a differential between a trigger signal and an occurrence of said reference signal and which one of a plurality of performance difficulty intervals the differential falls wherein ranges of the performance difficulty intervals established by difficulty data;

a commercially available consumer device separate from said timing unit, said consumer device comprising a computer and having an audible output and a visual output, said consumer device programmed with an application program that is adapted to decode data from said timing unit;

said application program adapted to provide occurrences of said reference signal with said audible output from decoded reference signal data;

said application program adapted to provide occurrences of said trigger signal from decoded response timing data to at least one chosen from said audio output and a visual output, the occurrences of the trigger signal from the decoded response timing data being a function of the differential between a trigger signal and an occurrence of said reference signal including which performance difficulty interval the differential falls to draw a user into synchronism with occurrences of the reference signal;

said consumer device generating control data used by said program to establish at least a value of said difficulty data; and a communication channel between said communication port and said consumer device, said communication channel communicating reference signal data and response timing data from said timing unit to said consumer device and control data from said consumer device to said communication port.

22. The timing system as claimed in claim 21 wherein said program having an interrupt generator, said interrupt generator being responsive to the trigger signal to interrupt the program in response to operation of the user input device and to record a value of the timer when the trigger signal occurs, wherein said circuit formats response timing data representing a relationship between the timer when the trigger signal occurs and one of the occurrences.

23. The timing system as claimed in claim 22 wherein said circuit includes another interrupt generator that is responsive to the timer and interrupts the program after passage of a defined period of time and wherein said circuit formats data representing an occurrence of a reference signal in response to the another interrupt generator.

24. The timing system as claimed in claim 21 wherein said programmable digital device comprises one chosen form a microprocessor, a programmable gate array, and an integrated circuit.

25. The timing system as claimed in claim 21 wherein said consumer device comprises a portable consumer device.

26. The timing system as claimed in claim 25 wherein said portable consumer device comprises one chosen from a laptop personal computer, a tablet computer, and a data phone.

27. The timing system as claimed in claim 21 wherein said reference signal data and response timing data are formatted into data packets.

28. The timing system as claimed in claim 21 wherein said application program controlling a manner in which at least one chosen from said audible output and said visual output is configured for presenting said relationship to a user.

29. The timing system as claimed in claim 21 wherein the performance difficulty intervals comprise an excellent band, an early band, a very early band, a late band, and a very late band.

30. The timing system as claimed in claim 21 wherein said timing unit comprises a housing having housing portions that house said circuit and said user input device, wherein relative motion between said housing portions operate said user input device.

31. The timing system as claimed in claim 30 wherein said circuit and said user input device are on a common circuit board.

* * * * *

UNITED STATES PATENT AND TRADEMARK OFFICE
CERTIFICATE OF CORRECTION

PATENT NO.            : 10,789,925 B2
APPLICATION NO.  : 15/659810
DATED                     : September 29, 2020
INVENTOR(S)         : Jose M. Hernandez, Jr.

It is certified that error appears in the above-identified patent and that said Letters Patent is hereby corrected as shown below:

In the Claims

Column 8
Line 37, Claim 6, delete "the" after --performance--

Signed and Sealed this
Sixteenth Day of August, 2022

Katherine Kelly Vidal
*Director of the United States Patent and Trademark Office*